(12) United States Patent
Kuyama et al.

(10) Patent No.: US 10,843,247 B2
(45) Date of Patent: Nov. 24, 2020

(54) MATERIAL PROPERTY VALUE ESTIMATING METHOD, MATERIAL PROPERTY VALUE ESTIMATING DEVICE, AND STEEL-STRIP MANUFACTURING METHOD

(71) Applicant: JFE STEEL CORPORATION, Tokyo (JP)

(72) Inventors: Shuji Kuyama, Tokyo (JP); Kazuya Asano, Tokyo (JP); Yoshitsugu Iijima, Tokyo (JP); Tomoyoshi Ogasahara, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 414 days.

(21) Appl. No.: 15/516,798

(22) PCT Filed: Oct. 10, 2014

(86) PCT No.: PCT/JP2014/077225
§ 371 (c)(1),
(2) Date: Apr. 4, 2017

(87) PCT Pub. No.: WO2016/056129
PCT Pub. Date: Apr. 14, 2016

(65) Prior Publication Data
US 2017/0297072 A1  Oct. 19, 2017

(51) Int. Cl.
*B21C 51/00* (2006.01)
*B21B 37/00* (2006.01)
(Continued)

(52) U.S. Cl.
CPC .............. *B21C 51/00* (2013.01); *B21B 37/00* (2013.01); *B21B 37/16* (2013.01); *B21B 37/74* (2013.01);
(Continued)

(58) Field of Classification Search
CPC ......... B21C 51/00; C22C 38/00; B21B 37/16; B21B 37/74; B21B 37/00; C21D 11/005;
(Continued)

(56) References Cited

U.S. PATENT DOCUMENTS 9,767,227 B2   9/2017  Sano et al.
2007/0106400 A1  5/2007  Mukhopadhyay
(Continued)

FOREIGN PATENT DOCUMENTS

CN   1431060 A   7/2003
CN   101391268 A  3/2009
(Continued)

OTHER PUBLICATIONS

International Search and Written Opinion for International Application No. PCT/JP2014/077225, dated Apr. 28, 2015, 5 pages.
(Continued)

*Primary Examiner* — Eric S. McCall
*Assistant Examiner* — Timothy P Graves
(74) *Attorney, Agent, or Firm* — RatnerPrestia

(57) ABSTRACT

A material-property-value estimating method of estimating a material-property-value of a target steel-strip product manufactured via at least one of a reheating process, a rolling process, and a cooling process, which are performed while a target material is being conveyed along a conveyance route, the material-property-value estimating method includes an estimating step of estimating a material-property-value of each of meshes dividing the target steel-strip product based on a measured value that has been measured once or more by a measuring device installed on the conveyance route, the measured value including at least a temperature of the target material; and a chemical composition per component of the target steel-strip product.

8 Claims, 7 Drawing Sheets

(51) Int. Cl.
| | |
|---|---|
| *G01N 25/00* | (2006.01) |
| *B22D 46/00* | (2006.01) |
| *C21D 11/00* | (2006.01) |
| *C22C 38/00* | (2006.01) |
| *B21B 37/16* | (2006.01) |
| *B21B 37/74* | (2006.01) |
| *B22D 11/22* | (2006.01) |
| *G01N 3/08* | (2006.01) |
| *G01N 33/20* | (2019.01) |
| *C21D 9/46* | (2006.01) |
| *C21D 9/573* | (2006.01) |

(52) U.S. Cl.
CPC .............. *B22D 11/22* (2013.01); *B22D 46/00* (2013.01); *C21D 11/00* (2013.01); *C21D 11/005* (2013.01); *C22C 38/00* (2013.01); *G01N 3/08* (2013.01); *G01N 25/00* (2013.01); *G01N 33/20* (2013.01); *C21D 9/46* (2013.01); *C21D 9/5735* (2013.01)

(58) Field of Classification Search
CPC ........ C21D 11/00; C21D 9/46; C21D 9/5735; G01N 3/08; G01N 25/00; G01N 33/20; B22D 11/22; B22D 46/00
See application file for complete search history.

(56) References Cited

U.S. PATENT DOCUMENTS

| | | | |
|---|---|---|---|
| 2009/0083206 A1* | 3/2009 | Shigemori | ........... G05B 19/418 706/46 |
| 2011/0103426 A1* | 5/2011 | Narihara | ................. B21C 51/00 374/121 |
| 2012/0019848 A1 | 1/2012 | Uemura | |
| 2015/0023387 A1 | 1/2015 | Narihara et al. | |
| 2015/0178415 A1* | 6/2015 | Sano | ........................ B21B 37/00 700/207 |

FOREIGN PATENT DOCUMENTS

| | | | |
|---|---|---|---|
| JP | 09272145 A | 10/1997 | |
| JP | 2005315703 A | 11/2005 | |
| JP | 2008055443 A | 3/2008 | |
| JP | 2008296251 A | 12/2008 | |
| JP | 2009020807 A | 1/2009 | |
| JP | 2009070227 A | 4/2009 | |
| JP | 2010033536 A | 2/2010 | |
| JP | 2010214432 A | 9/2010 | |
| JP | 2012027638 A | 2/2012 | |
| JP | 2012027683 A | 2/2012 | |
| JP | 2012166264 A | 9/2012 | |
| JP | 2014018844 A | 2/2014 | |
| WO | PCT/JP2012/072234 | * 8/2012 | ............. G06F 17/50 |
| WO | 2014033928 A1 | 3/2014 | |

OTHER PUBLICATIONS

Notification of Reasons for Refusal for Japanese Application No. 2015-534855, dated Jun. 3, 2016 with Concise Statement of Relevance, 3 pages.
Decision of Refusal of Japanese Application for Japanese Application No. 2015-534855, dated Aug. 24, 2016 with Concise Statement of Relevance, 3 pages.
Extended European Search Report for European Application No. 14 903 581.8, dated May 2, 2018, 9 pages.
Chinese Office Action for Chinese Application No. 201480082515.9, dated Dec. 27, 2017 with English Searth Report, 13 pages.
Korean Office Action for Korean Application No. 10-2017-7009503, dated Feb. 28, 2018, including Concise Statement of Relevance of Office Action, 9 pages.
European Communication pursuant to Article 94(3) for European Application No. 14 903 581.8, dated Nov. 12, 2019, 10 pages.

* cited by examiner

FIG.2

| PRODUCT NO. | MESH NO. | MANUFACTURING CONDITIONS ||||||| MATERIAL PROPERTY [Mpa] |
| | | CHEMICAL COMPOSITION [%] || THICKNESS AND WIDTH HISTORY [mm] ||| TEMPERATURE HISTORY [°C] || SPEED HISTORY [mpm] || |
| | | VALUE OF COMPONENT 1 | VALUE OF COMPONENT 2 ... | THICKNESS 1 | THICKNESS 2 | ... WIDTH 1 ... | TEMPERATURE 1 | TEMPERATURE 2 ... | SPEED 1 | SPEED 2 ... | |
|---|---|---|---|---|---|---|---|---|---|---|---|
| S0001 | P01_001 | 2.0 | 0.1 | 25 | 3 | | 1200 | 700 | 600 | 800 | 980 |
| S0001 | P01_002 | 2.0 | 0.1 | 25 | 3 | | 1221 | 698 | 600 | 800 | 991 |
| ... | ... | ... | ... | ... | ... | | ... | ... | ... | ... | ... |
| S0002 | P01_001 | 1.5 | 0.3 | 15 | 2 | | 1240 | 811 | 555 | 570 | — |
| ... | ... | ... | ... | ... | ... | | ... | ... | ... | ... | ... |

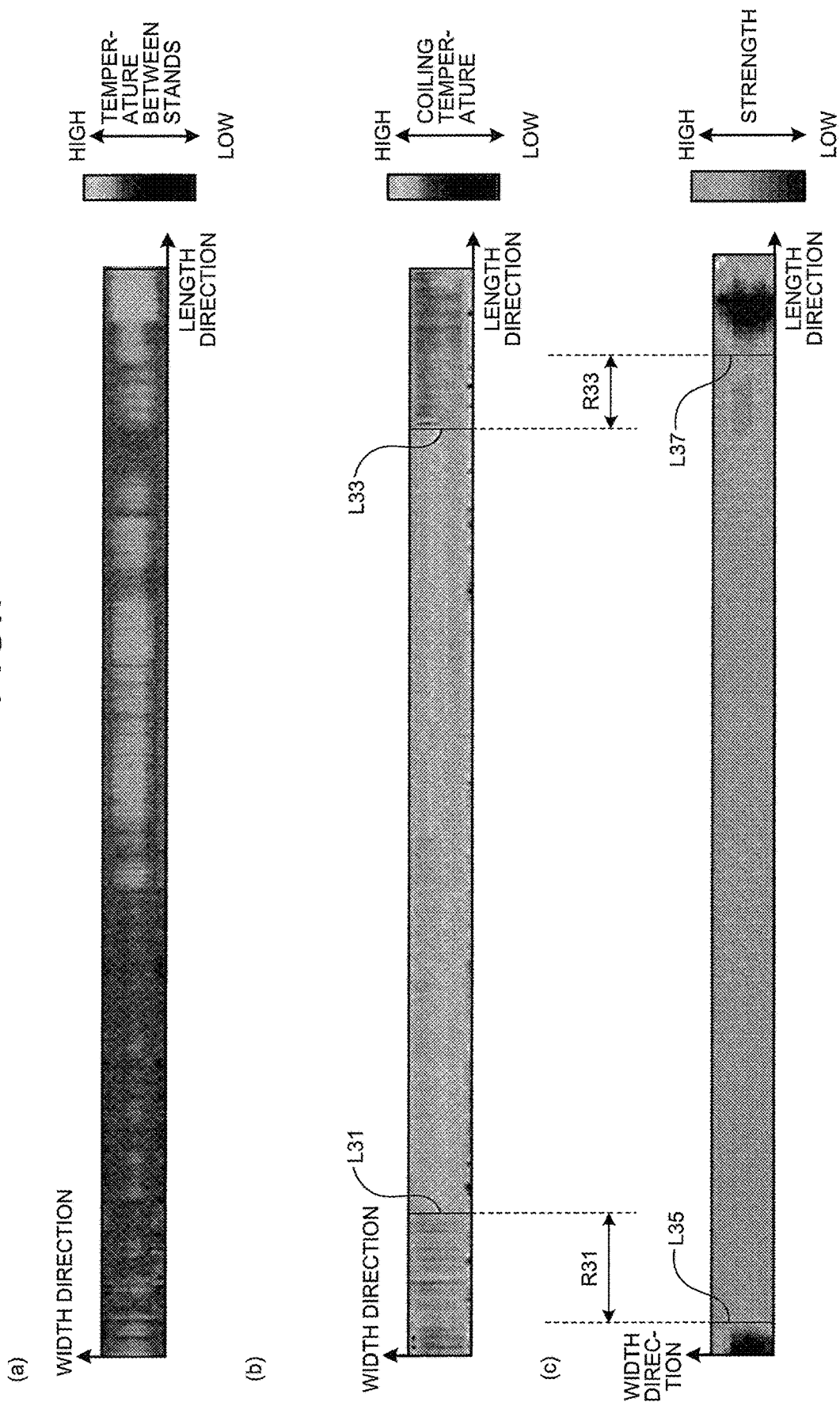

MATERIAL PROPERTY VALUE ESTIMATING METHOD, MATERIAL PROPERTY VALUE ESTIMATING DEVICE, AND STEEL-STRIP MANUFACTURING METHOD

CROSS REFERENCE TO RELATED APPLICATIONS

This is the U.S. National Phase application of PCT International Application No. PCT/JP2014/077225, filed Oct. 10, 2014. The disclosure of this application being incorporated herein by reference in its entirety for all purposes.

FIELD OF THE INVENTION

The present invention relates to a material property value estimating method and a material property value estimating apparatus for estimating material properties of a steel-strip, and to a method of manufacturing a steel-strip.

BACKGROUND OF THE INVENTION

Steel-strip products manufactured via processes including a reheating process, a forming process, and a cooling process are delivered to customers as coils, or sent to a subsequent process in order to be processed further. In order to guarantee the quality required (material properties including strength), quality assessment of such steel-strip products is performed before the delivery or the like. In general, since the quality of a steel-strip product is not stable at end portions thereof, the quality of the whole product is maintained by cut-off positions being determined from results of the quality assessment and the end portions being cut off.

For example, as a technique for assessing the quality, a technique has been known, in which the temperature is measured by the entire area of a hot-rolled metal strip being imaged by a near infrared camera (thermography) and the quality is assessed based on the measured temperature distribution (see Patent Literature 1).

CITATION LIST

Patent Literature

Patent Literature 1: Japanese Laid-open Patent Publication No. 2008-296251

SUMMARY OF THE INVENTION

However, since the above mentioned technique of Patent Literature 1 focuses on a correlation between the quality (material property value) and the temperature of the hot-rolled metal strip, and the quality is assessed by use of the temperature as an index; influence of factors other than the temperature on the quality is unable to be considered, and accuracy of the quality assessment has been insufficient in some cases. Further, as a result, there has been a problem that the cut-off positions are unable to be determined appropriately, and thus the cut-off is performed with an inferior quality portion (an area with a disqualified material property value) being left behind, or on the contrary, even a satisfactory quality portion (an area with a qualified material property value) is also cut off and the yield is decreased.

The present invention has been made in view of the above, and object thereof is to provide a material property value estimating method and a material property value estimating apparatus, which enable material properties of a steel-strip to be estimated accurately. Further, another object of the present invention is to provide a method of manufacturing a steel-strip, the method enabling decrease in the yield to be reduced.

To solve the problem and achieve the object, a material property value estimating method of estimating a material property value of a target steel-strip product manufactured via at least one of a reheating process, a rolling process, and a cooling process, which are performed while a target material is being conveyed along a conveyance route according to the present invention is a method of estimating a material property value of each of meshes dividing the target steel-strip product based on a measured value that has been measured once or more by a measuring device installed on the conveyance route, the measured value including at least a temperature of the target material; and a chemical composition per component of the target steel-strip product Moreover, a material property value estimating apparatus that estimates a material property value of a target steel-strip product manufactured via at least one of a reheating process, a rolling process, and a cooling process, which are performed while a target material is being conveyed along a conveyance route according to the present invention includes: an estimating means that estimates a material property value of each of meshes dividing the target steel-strip product, based on: a measured value that has been measured once or more by a measuring device installed on the conveyance route, the measured value including at least a temperature of the target material; and a chemical composition per component of the target steel-strip product.

Moreover, a method of manufacturing a steel-strip manufactured via at least one of a reheating process, a rolling process, and a cooling process, which are performed while a target material is being conveyed along a conveyance route according to the present invention includes: an estimating step of estimating a material property value of each of meshes dividing the steel-strip based on: a measured value that has been measured once or more by a measuring device installed on the conveyance route, the measured value including at least a temperature of the target material; and a chemical composition per component of the steel-strip; and a cutting step of determining a boundary position between a qualified portion and a disqualified portion in the steel-strip by performing threshold processing of the estimated material property value of each of the meshes, and cutting the steel-strip at the determined boundary position.

Moreover, a method of manufacturing a steel-strip manufactured via at least one of a reheating process, a rolling process, and a cooling process, which are performed while a target material is being conveyed along a conveyance route according to the present invention includes: an estimating step of estimating a material property value of each of meshes dividing the target steel-strip product based on: a measured value that has been measured once or more by a measuring device installed on the conveyance route, the measured value including at least a temperature of the target material; and a chemical composition per component of the target steel-strip product; and a manufacturing condition determining step of changing one or more settings of manufacturing conditions of the steel-strip, based on a difference between the estimated material property value of each of the meshes and a required specification of material property value.

According to the present invention, material properties of a steel-strip are able to be estimated accurately. Further, according to the present invention, decrease in the yield of a steel-strip manufacturing process is able to be reduced.

BRIEF DESCRIPTION OF DRAWINGS

FIG. 2 is a diagram illustrating an example of a data configuration of an actual result database.

FIG. 7 is a diagram illustrating a temperature distribution of temperature during cooling (a), a temperate distribution of temperature after cooling (b), and a material property value image (c).

DETAILED DESCRIPTION OF EMBODIMENTS OF THE INVENTION

Figure 1:
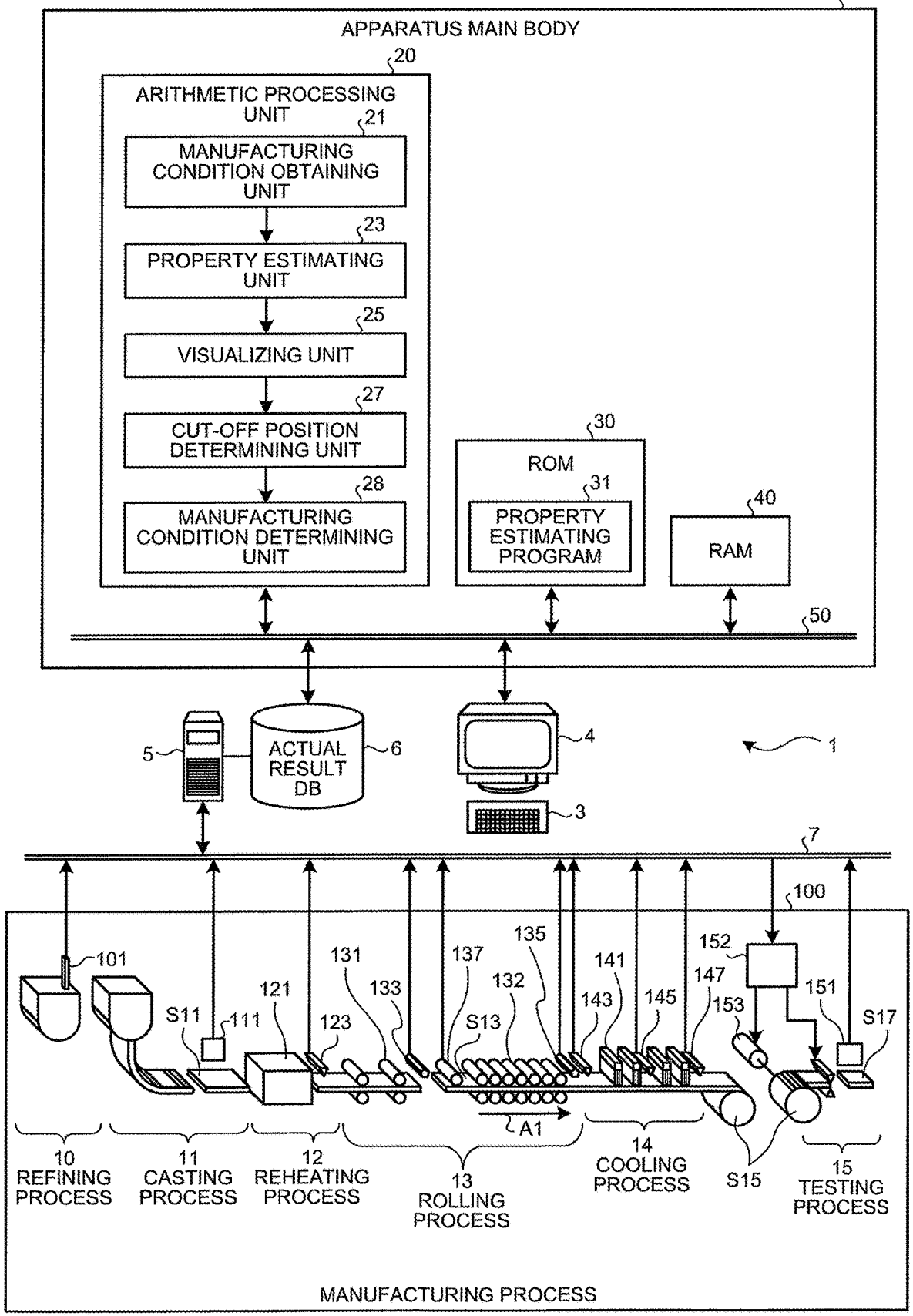
FIG. 1 is a schematic diagram illustrating an example of an overall configuration of a material property value estimating apparatus, and a manufacturing process, to which this material property value estimating apparatus is applied.

Hereinafter, with reference to the drawings, a mode for implementing a material property value estimating apparatus and a material property value estimating method of the present invention will be described. The present invention is not limited by this embodiment. Further, in the drawings, the same portions will be illustrated with the same signs appended thereto.

FIG. 1 is a schematic diagram illustrating an example of an overall configuration of a material property value estimating apparatus 1 of this embodiment, and a manufacturing process 100, to which this material property value estimating apparatus 1 is applied.

First of all, the manufacturing process 100 will be described. As illustrated in FIG. 1, the manufacturing process 100 includes: a refining process 10; a casting process 11; a reheating process 12; a rolling process 13 as a forming process; a cooling process 14, and a testing process 15. Facilities for implementing the reheating process 12, the rolling process 13, and the cooling process 14, of these respective processes 10 to 15, are installed on a conveyance route of a target material (a slab S11 or a rolled material S13), the conveyance route formed by table rolls (not illustrated) being laid thereon; and carry out reheating, rolling, and cooling of the slab S11 or the rolled material S13 sequentially conveyed in a conveyance direction A1 on the conveyance route.

The refining process 10 is a process of adjusting and adding weights of component elements (chemical composition) to steel in a liquid state, and thereby forming steel of a predetermined composition. In this refining process 10, a component measuring device 101 is installed, and the adjusted chemical composition (actual value) per component of steel is measured. The measured chemical composition per component is output at any time to an actual value collecting device 5 described later.

The subsequent casting process 11 is a process of: cooling the steel in the liquid state, the steel having been adjusted to the above mentioned predetermined composition; casting the steel in a plate shape; and cutting the steel by a predetermined length into the slab S11. In this casting process 11, a thickness meter 111 is installed, and thickness of the slab S11 (slab thickness) is measured. The measured slab thickness is output at any time to the actual value collecting device 5.

The subsequent reheating process 12 is a process of reheating the slab S11 with a heating furnace 121 to near 1250° C. In this reheating process 12, for example, a thermometer 123 is installed at an outlet side of the heating furnace 121, and surface temperature (delivery temperature of reheating process) of the slab S11 at the time of completion of reheating when the installation location is passed is continuously measured. The measured delivery temperature of reheating process is output at any time to the actual value collecting device 5.

The subsequent rolling process 13 is a process of stepwisely rolling the rolled material (the slab that has finished being reheated) S13 with plural rolling mill rolls 131 and 132, specifically, the rolling mill rolls 131 constituting roughers and the rolling mill rolls 132 constituting finishers; and the slab thickness of about 250 mm is rolled thinly to about 1 mm to 20 mm. In this rolling process 13, as dimension meters, for example, a thickness and width meter 133 is installed in the middle of rolling, such as between the roughers and the finishers, and a thickness and width meter 135 is installed at an outlet side of the finishers. In this rolling process 13, thickness (thickness between stands) and width (width between stands) of the rolled material S13 when the rolled material S13 passes the installation location of the thickness and width meter 133, and thickness (finishing thickness) and width (finishing width) of the rolled material S13 when the rolled material S13 passes the installation location of the thickness and width meter 135 are measured continuously. Further, in the rolling process 13, for example, a measuring roll 137, which is a speed meter, is installed in the middle of rolling, such as between the roughers and the finishers, and conveyance speed (conveyance speed upon rolling) of the rolled material S13 in the rolling process 13 is continuously measured. The thickness between stands, the finishing thickness, the width between stands, the finishing width, and the conveyance speed upon rolling, which have been measured, are output at any time to the actual value collecting device 5.

The subsequent cooling process 14 is a process of supplying cooling water to the rolled material S13 that has finished being rolled, and cooling the rolled material S13 to several hundred degrees Celsius, by use of plural coolants 141. In this cooling process 14, for example, a thermometer 143 is installed at an inlet side of the most upstream coolant 141, a thermometer 145 is installed in the middle of cooling between the coolants 141, and a thermometer 147 is installed at an outlet side of the most downstream coolant 141. In this cooling process 14, surface temperature (entry temperature of cooling process) of the rolled material S13 passing the thermometer 143, surface temperature (temperature during cooling) of the rolled material S13 passing the thermometer 145, and surface temperature (temperature after cooling) of the rolled material S13 passing the thermometer 147 are measured continuously. Further, in the cooling process 14, a tachometer (not illustrated) as a speed meter is installed at an appropriate location, such as in the middle of cooling, and conveyance speed of the rolled material S13 in the cooling process 14 (conveyance speed upon cooling) is continuously measured by the number of rotations of the table rolls being measured and converted into speed. The entry temperature of cooling process, the temperature during cooling, the temperature after cooling, and the conveyance speed upon cooling, which have been measured, are output at any time to the actual value collecting device 5.

A steel-strip product that has been manufactured by finishing being subjected up to the cooling process 14 as described above is coiled up by a coiler (not illustrated) into a coil S15. The subsequent testing process 15 is a process of performing a tension test on a steel piece (test piece) S17 sampled from an end portion or the like of the steel-strip product (coil) S15 by uncoiling the steel-strip product (coil) S15; and yield strength (YS), tension strength (TS), and elongation (EL) of the steel piece S17 are measured by a tester 151. The respective values of the yield strength YS, the tension strength TS, and the elongation EL, which have been measured, are output at any time as material properties (actual values), together with a sampling position of the steel piece S17 in the steel-strip product S15, to the actual value collecting device 5.

The number of installed thermometers and their installation locations in the reheating process 12 and the cooling process 14 are not limited to the above described number of installed thermometers and the installation locations, and at least one thermometer is preferably installed in each of the respective processes 12 and 14. Further, the number of installed thickness and width meters and their installation locations in the rolling process 13 are similarly not limited to the number of installed thickness and width meters and their installation locations described above, and at least one thickness and width meter is preferably installed. However, in order to accurately estimate material properties described later, all of temperatures of the rolled material S3 before cooling, in the middle of cooling, and at the time of completion of cooling in the cooling process 14 (the entry temperature of cooling process, the temperature during cooling, and the temperature after cooling) are desirably obtained. Further, the rolled material processed in the processes from the heating furnace 121 to the coiler S15 is not limited to a single rolled material as described above, and plural rolled materials may be processed.

Further, the measurement of temperature of the slab S11 or the rolled material S13 by the thermometer 123, 143, 145, or 147 is desirably performed over the entire width direction range of the slab S11 or the rolled material S13 passing the installation location thereof, but a configuration may be adopted, in which temperature of a part of the width direction range is measured. Similarly, the measurement of thickness and width of the slab S11 or the rolled material S13 by the thickness meter 111 or the thickness and width meter 133 or 135 is desirably performed over the entire width direction range of the slab S1 or the rolled material S13 passing the installation location thereof, but a configuration may be adopted, in which the thickness and width are measured for a part of the width direction range.

The material property value estimating apparatus 1 applied to this manufacturing process 100 is configured by: an apparatus main body 2, an input device 3, a display device 4, the actual value collecting device 5 serving as a collecting means, and an actual result DB 6 serving as an actual result data storage means, being connected to one another to be able to transmit and receive data via a transmission bus 7 and a bus wiring 50 that connects between respective units in the apparatus main body 2.

The apparatus main body 2 is realized by use of a general-purpose information processing device, such as a personal computer or a work station, and includes an arithmetic processing unit 20, a ROM 30, and a RAM 40.

The arithmetic processing unit 20 is realized by hardware, such as a CPU. This arithmetic processing unit 20 integrally controls operation of the whole material property value estimating apparatus 1 by performing instruction, data transfer, and the like to the respective units constituting the material property value estimating apparatus 1; based on programs and data stored in the ROM 30, operation signals input from the input device 3, various types of information and the like obtained from the actual value collecting device 5 and the actual result DB 6. This arithmetic processing unit 20 includes, as main functional units, a manufacturing condition obtaining unit 21, a property estimating unit 23 serving as an estimating means, a visualizing unit 25 serving as a display processing means, and a cut-off position determining unit 27 serving as a determining means.

In the ROM 30: programs for causing the material property value estimating apparatus 1 to operate and realizing various functions that this material property value estimating apparatus 1 includes; data used during execution of these programs; and the like, are stored. Further, a property estimating program 31 is stored therein, the property estimating program 31: causing the arithmetic processing unit 20 to function as the manufacturing condition obtaining unit 21, the property estimating unit 23, the visualizing unit 25, and the cut-off position determining unit 27; and visualizing material properties of the steel-strip product S15 after estimating the material properties.

The RAM 40 is a semiconductor memory used as a working memory of the arithmetic processing unit 20; and includes a memory space that temporarily holds therein the programs executed by the arithmetic processing unit 20, data used during execution thereof, and the like.

The input device 3 is realized by an input device, such as, for example, a keyboard and a mouse, a touch panel, or various switches; and outputs input signals according to input of operation to the apparatus main body 2. The display device 4 is realized by a display device, such as an LCD, an EL display, or a CRT display; and displays thereon various screens based on display signals input from the apparatus main body 2.

The actual value collecting device 5 may be realized by a known hardware configuration including: an arithmetic unit, such as a CPU; a main storage device; an auxiliary storage device, such as a hard disk or any of various storage media; a communication device; a display device; an input device; and the like, and for example, a general-purpose computer, such as a server computer, a work station, or a personal computer, may be used as the actual value collecting device 5. This actual value collecting device 5 is connected, via the transmission bus 7, to the measuring devices in the manufacturing process 100, such as the component measuring device 101 of the refining process 10, the thickness meter 111 of the casting process 11, the thermometer 123 of the reheating process 12, the thickness and width meters 133 and 135 and the measuring roll 137 of the rolling process 13, the thermometers 143, 145, and 147 of the cooling process 14, and the tester 151 of the testing process 15, which have been described above. The actual value collecting device 5 collects measured values of: the chemical composition per component; the slab thickness; the thickness between stands; the finishing thickness; the width between stands; the finishing width; the delivery temperature of reheating process; the entry temperature of cooling process; the temperature during cooling; the temperature after cooling; the conveyance speed upon reheating; the conveyance speed upon rolling; the conveyance speed upon cooling; and the material properties, which have been measured by these measuring devices; and performs, based on the collected measured values, a process of registering actual result data of the steel-strip product S15 sequentially manufactured in the manufacturing process 100 into the actual result DB 6 (actual result data registration process).

The actual result DB 6 is a database (DB) accumulating therein actual result data of steel-strip products manufactured in the past by the manufacturing process 100, and is constructed by actual result data being registered and updated every time the steel-strip product S15 is manufactured by the manufacturing process 100 (storage step). FIG. 2 is a diagram illustrating an example of a data configuration of the actual result DB 6. Set as an individual set of actual result data is: measured values collected by the actual value collecting device 5, the measured values being values of predetermined manufacturing conditions and material properties; or estimated values estimated based on these measured values. Specifically, as illustrated in FIG. 2, each set of actual result data is composed of manufacturing conditions 65 associated with a combination of a product number 61 and a mesh number 63, and a material property value 67. The product number 61 is an identification number for identifying that steel-strip product, and the mesh number 63 indicates a position in the steel-strip product corresponding to a target of measurement of measured values corresponding thereto (see FIG. 3 described later).

The manufacturing conditions 65 are composed of values per manufacturing condition item, and in this embodiment, include a chemical composition 651, a thickness and width history 653, a temperature history 655, and a speed history 657. In the chemical composition 651, measured values of the chemical composition per component are set as a component 1, a component 2, and so on. Types of components differ depending on the steel-strip products, and representative examples include carbon (C), manganese (Mn), silicon (Si), and aluminum (Al). In the thickness and width history 653, measured values of the slab thickness, the thickness between stands, the finishing thickness, and the like are set as a thickness 1, a thickness 2, and so on, and measured values of the width between stands, the finishing width, and the like are set as a width 1, and so on. In the temperature history 655, measured values or estimated values of the delivery temperature of reheating process, the entry temperature of cooling process, the temperature during cooling, the temperature after cooling, and the like are set as a temperature 1, a temperature 2, and so on. In the speed history 657, measured values of the conveyance speed upon reheating, the conveyance speed upon rolling, the conveyance speed upon cooling, and the like are set as a speed 1, a speed 2, and so on. In the material property value, a measured value or an estimated value thereof is set.

Next, flows of processes performed in the material property value estimating apparatus 1 configured as described above will be described. First, the actual result data registration process will be described. In this actual result data registration process, from when manufacturing of a steel-strip product (target steel-strip product) manufactured at that time is started to when the manufacturing is finished, the actual value collecting device 5 collects measured values measured at any time by the measuring devices in the respective processes 10 to 14 in the manufacturing process thereof (collecting step).

Figure 3:
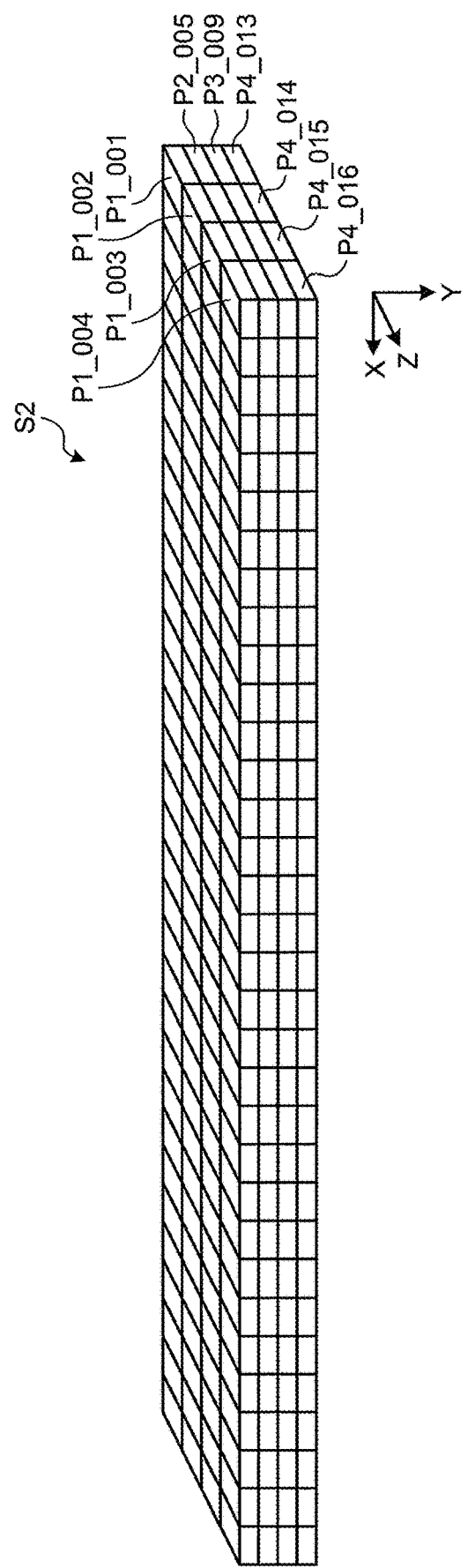
FIG. 3 is a diagram illustrating a target steel-strip product.

FIG. 3 is a diagram illustrating a target steel-strip product S2 that has finished being manufactured. As illustrated in FIG. 3, when the target steel-strip product S2 that has finished being manufactured is uncoiled from a coiled state, a total length thereof is a length corresponding to a coiling amount, and the uncoiled target steel-strip product S2 has a strip shape with a thickness of the finishing thickness and a width of the finishing width. Hereinafter, a length direction of the target steel-strip product S2 will be defined as an X-direction, a thickness direction thereof as a Y-direction, and a width direction thereof as a Z-direction.

Of the manufacturing process 100, in the reheating process 12, the rolling process 13, and the cooling process 14, which are performed while the target material is being conveyed, measured values by the measuring devices in the respective processes 12 to 14 are obtained while measurement positions thereof are being tracked. Examples of a measurement position tracking means include: a method of identifying, based on the number of times a walking beam is moved, a measurement position, the walking beam conveying the target material in the heating furnace in the reheating process 12; a method of detecting a measurement position by using y rays in the rolling process 13; a method of estimating, based on the number of rotations of a rolling mill in the rolling process 13, a measurement position; and a method of estimating a measurement position by counting the number of rotations of the coiler in the cooling process 14. As a result, the measured values of the thickness between stands, the finishing thickness, the width between stands, the finishing width, the delivery temperature of reheating process, the entry temperature of cooling process, the temperature during cooling, the temperature after cooling, the conveyance speed upon reheating, the conveyance speed upon rolling, and the conveyance speed upon cooling, which are measured in the respective processes 12 to 14, are ultimately collected for each of measurement positions corresponding to respective meshes of the meshed top layer illustrated in FIG. 3, for example. An X-direction width of this mesh corresponds to a measurement period of the measuring devices in the respective processes 12 to 14.

In the actual result data registration process, the actual value collecting device 5 divides the target steel-strip product S2 in the Y-direction also as illustrated in FIG. 3, and allocates unique mesh numbers to all of the meshes. In FIG. 3, mesh numbers allocated to some of the meshes are illustrated as an example. The size of the meshes is not particularly limited, may be a size corresponding to the above mentioned measurement period, and is, for example, a size resulting from division in each of the X-direction, the Y-direction, and the Z-direction by a width in a range of, for example, from several tens of micrometers to several meters.

The mesh number is allocated as, for example, a character string, which is a combination of a layer number and a serial number consecutively numbering each mesh, with an underbar, "_", interposed therebetween. The layer number is for identifying a position of a layer of each mesh. In FIG. 3, meshes of four layers resulting from division into four in the Y-direction are illustrated, and their layer numbers in order from the top layer are "P1", "P2", "P3", and "P4". The Y-direction is not necessarily divided, and if the finishing thickness of the target steel-strip product is small, the meshes may be singly layered.

The actual value collecting device 5 associates the values of the manufacturing condition items including the measured values by the measuring devices in the respective processes 12 to 14 with each of the meshes, into which the target steel-strip product S2 is divided as described above, to form one set of actual result data, and registers the one set of actual result data into the actual result DB 6.

When explanation is made in order, the chemical composition per component, of the values of the manufacturing condition items of each mesh, is, for example, uniformly the measured values measured by the component measuring device 101. Similarly, the slab thickness is, for example, the measured values measured by the thickness meter 111 for all of the meshes.

Further, the values of the thickness between stands, the finishing thickness, the width between stands, the finishing width, the delivery temperature of reheating process, the entry temperature of cooling process, the temperature during cooling, the temperature after cooling, the conveyance speed upon reheating, the conveyance speed upon rolling, and the conveyance speed upon cooling, the values for the meshes of the top layer having the layer number, "P1", are the measured values at the corresponding measurement positions obtained while tracking is being performed, as described above. Such values for meshes of the lower layers with the layer numbers, "P2", "P3", and "P4", are the same values as the measured values of the respective meshes of the top layer, or estimated values estimated from these measured values. Specifically, the values of the thickness between stands, the finishing thickness, the width between stands, the finishing width, the conveyance speed upon reheating, the conveyance speed upon rolling, and the conveyance speed upon cooling are the measured values for the meshes of the top layer with the same X-direction and X-direction positions. Further, the values of the delivery temperature of reheating process, the entry temperature of cooling process, the temperature during cooling, and the temperature after cooling are, for example, estimated values obtained as a result of performing a process of estimating respective values of the delivery temperature of reheating process, the entry temperature of cooling process, the temperature during cooling, and the temperature after cooling at positions of the respective meshes of the lower layers by use of a heat transfer model or the like defined in advance based on the measured values of the respective meshes of the top layer.

Since the material properties are estimated by a material property value estimating process described later (Step a11 in FIG. 4) or measured in the testing process 15 of the later stage, values thereof are not set herein.

Figure 4:
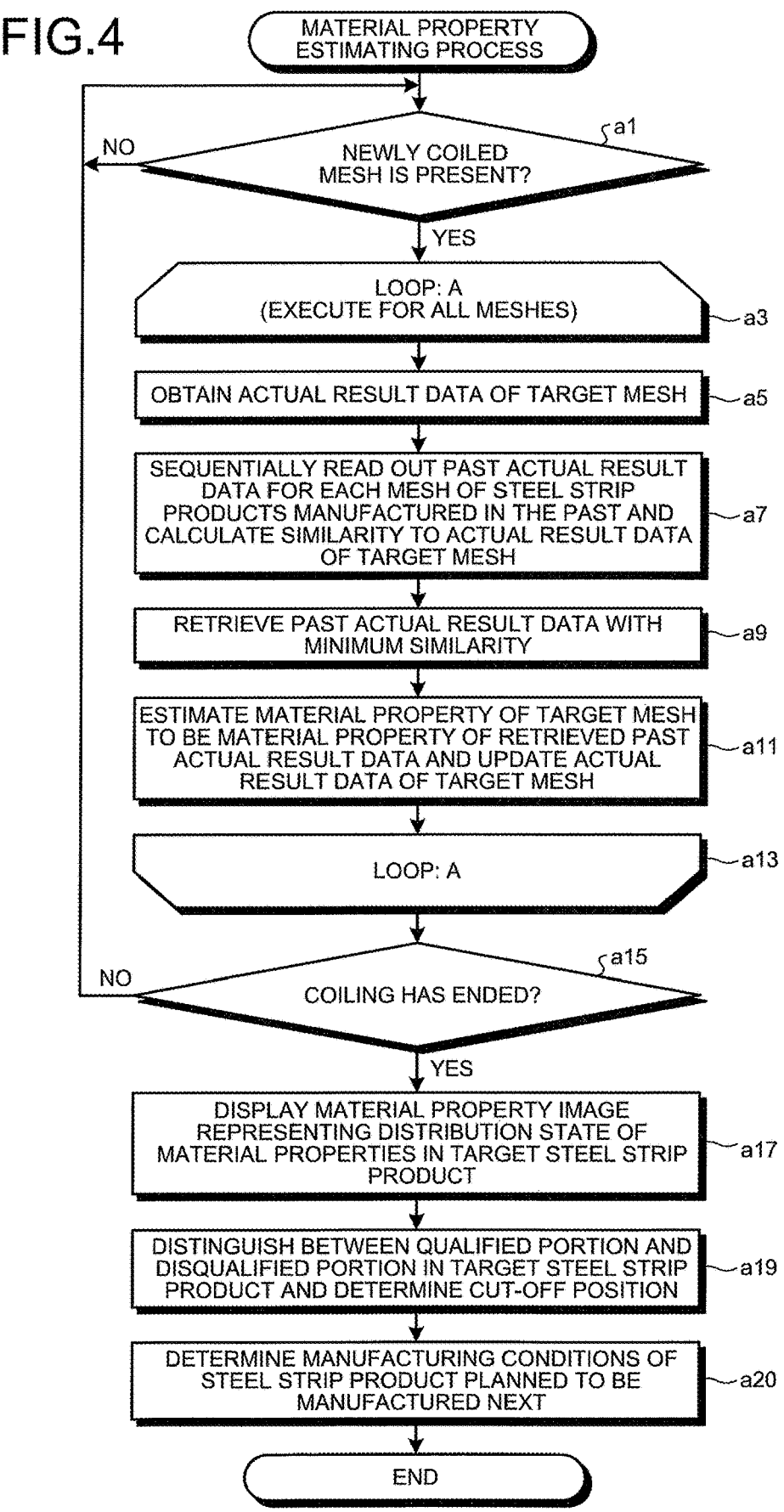
FIG. 4 is a flow chart illustrating a procedure of a material property value estimating process.

Next, the material property value estimating process will be described. FIG. 4 is a flow chart illustrating a procedure of the material property value estimating process executed by the arithmetic processing unit 20 in the apparatus main body 2. In the material property value estimating apparatus 1, the material property value estimating method is implemented, by the actual value collecting device 5 executing the above described actual result data registration process and the arithmetic processing unit 20 executing the material property value estimating process according to the procedure in FIG. 4. The material property value estimating process may be realized by the arithmetic processing unit 20 reading and executing the property estimating program 31 stored in the ROM 30. This material property value estimating process is started when the coiler starts coiling up the target steel-strip product.

That is, the arithmetic processing unit 20 determines presence or absence of a mesh that has finished being manufactured by being newly coiled up by the coiler. If a mesh that has finished being manufactured is present, that is, every time an amount worth an X-direction width of a mesh is coiled up by the coiler (Step a1; Yes), the arithmetic processing unit 20 executes a process of a loop A for all of meshes that have finished being manufactured in order, the meshes being target meshes (Step a3 to Step a13). Since the steel-strip product manufactured by the manufacturing process 100 is long with a total length thereof being about 1000 meters, and the steel-strip product is coiled up by the coiler from a distal end side that has finished being manufactured first (for which up to the cooling process 14 has been completed); for a while after the coiling by the coiler is started, a portion that has been coiled up as a coil after finishing being manufactured and a portion in the middle of manufacturing (for which up to the cooling process 14 has not been completed) coexist with each other.

For example, when a distal end of the target steel-strip product illustrated in FIG. 3 has started to be coiled up by the coiler and an amount worth an X-direction width of a mesh has been coiled up, the process of the loop A is executed for each of sixteen meshes at the right end, the sixteen meshes sequentially being the target meshes.

That is, in the loop A, first, the manufacturing condition obtaining unit 21 reads and obtains actual result data (hereinafter, referred to as "target actual result data") of a target mesh from the actual result DB 6, based on a product number of the target steel-strip product and a mesh number of the target mesh (Step a5).

Subsequently, the property estimating unit 23 estimates a material property value of the target mesh by executing the processing of Step a7 to Step a11 (estimating step). That is, the property estimating unit 23 first sequentially reads the actual result data (hereinafter, referred to as "past actual result data") for each mesh related to steel-strip products manufactured in the past from the actual result DB 6, and calculates similarity between the respective data of the target actual result data and the past actual result data by comparing the values for each manufacturing condition item between the read actual result data and the target actual result data obtained in Step a5 (Step a7). For example, according to the following Equation (1), the property estimating unit 23 sequentially calculates, as the similarity to the corresponding past actual result data, a sum of squares of differences between values, each of the differences being a difference between values of the target actual result data and the past actual result data for each manufacturing condition item. By this process, the similarity is calculated as a smaller value when the past actual result data have values per manufacturing condition item that are similar, as a whole, to the target actual result data and thus manufacturing conditions similar to the target mesh, and as a larger value for the other past actual result data.

$$\text{Similarity} = \tag{1}$$
$$\alpha_{11} \times \left( \begin{array}{c} \text{Value of component 1 of target actual result data} - \\ \text{Value of component 1 of past actual result data} \end{array} \right)^2 +$$
$$\alpha_{12} \times \left( \begin{array}{c} \text{Value of component 2 of target actual result data} - \\ \text{Value of } \textit{conponent } 2 \text{ of past actual result data} \end{array} \right)^2 +$$
$$\vdots$$
$$\alpha_{21} \times \left( \begin{array}{c} \text{Value of thickness 1 of target actual result data} - \\ \text{Value of thickness 1 of past actual result data} \end{array} \right)^2 +$$
$$\vdots$$
$$\alpha_{31} \times \left( \begin{array}{c} \text{Value of width 1 of target actual result data} - \\ \text{Value of width 1 of past actual result data} \end{array} \right)^2 +$$
$$\vdots$$
$$+ \alpha_{41} \times \left( \begin{array}{c} \text{Value of temperature 1 of target actual result data} - \\ \text{Value of temperature 1 of past actual result data} \end{array} \right)^2$$
$$\vdots$$

The equation for calculating the similarity expressed by the above Equation (1) is just an example, and is not limited to this example. That is, the equation for calculating the similarity is any equation expressing that the more similar the manufacturing conditions of the past actual result data are to those of the target mesh, the smaller the numerical value becomes.

Further, herein, the similarity to the target actual result data is calculated for all of the past actual result data registered in the actual result DB 6. On the contrary, based on a mesh number of the target actual result data, actual result data of mesh numbers having the same layer number may be elected, and similarities may be calculated for the elected actual result data. Thereby, the material property value is able to be estimated by retrieving the one which is smaller in the similarity from manufacturing conditions of the same layer.

Thereafter, the property estimating unit 23 retrieves, based on the similarities calculated in Step a7, past actual result data having the minimum similarity from the past actual result data (Step a9). The property estimating unit 23 then estimates a material property value of the target mesh to be the material property value of the retrieved past actual result data, and updates the actual result data of the target mesh (Step a11). Thereafter, the process of the loop A for the target mesh is ended. By this process and the above described actual result data registration process, the material property value estimating apparatus 1 functions as a registration means.

As described above, a steel piece is sampled from the target steel-strip product manufactured, a material property value thereof is measured, and the measured value is output to the actual value collecting device 5 in the testing process 15 after the cooling process 14, and in this case, the actual value collecting device 5 updates the material property value of the mesh that the sampling position of the steel piece belongs, with the measured value.

Further, a technique used in the estimation of the material properties of the target meshes is not limited to the above described technique of using similarity. For example, material properties of target meshes may be estimated from past actual result data by use of another technique, such as regression or interpolation.

When the coiler has finished coiling up the target steel-strip product and the process of loop A has been executed for all of the meshes (Step a15; Yes), subsequently, the visualizing unit 25 executes a process of generating a material property value image representing a distribution state of material properties in the target steel-strip product for each mesh layer and displaying the material property value image on the display device 4 (Step a17). For example, the visualizing unit 25 reads the material property value of each mesh of the target steel-strip product per layer from the actual result DB 6, and executes the process of generating and displaying, as the material property value image, a contour graph for each layer, the contour graph depicting meshes with the same material property value in the same color.

Figure 5:
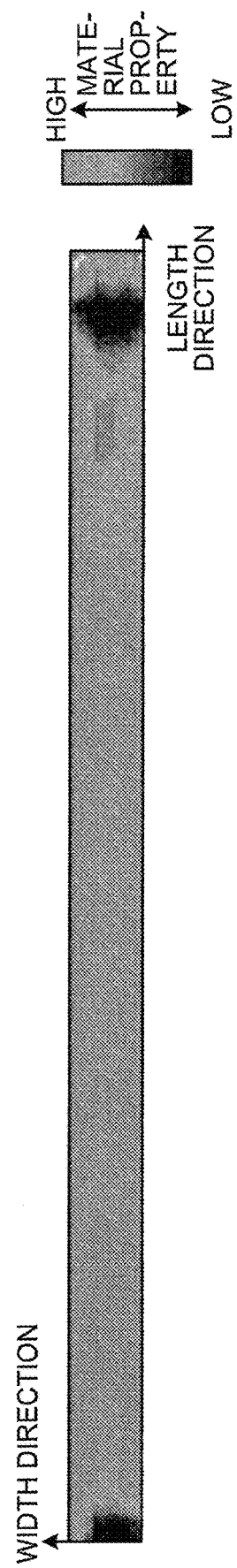
FIG. 5 is a diagram illustrating an example of a material property value image.

FIG. 5 is a diagram illustrating an example of the material property value image, and illustrates a material property value image of the top layer with the layer number P1, with a horizontal direction thereof being a length direction of the target steel-strip product and a vertical direction thereof being a width direction of the target steel-strip product. At Step a17 in FIG. 4, the material property value images of the respective layers, the material property value images representing the distribution states of the material properties in the target steel-strip product as illustrated in FIG. 5, are displayed on the display device 4 side by side, or according to input of operation by an operator, a material property value image of one of the layers is selectively displayed and presented to the operator.

Subsequently, the cut-off position determining unit 27 determines a cut-off position of the target steel-strip product (Step a19). Specifically, the cut-off position determining unit 27 firstly performs threshold processing of the property value of each mesh of the target steel-strip product by using, as a threshold, a permissible value of material property value defined according to required quality in advance, and distinguishes between a qualified portion where the material properties are not less than a threshold, and a disqualified portion. The cut-off position determining unit 27 then determines a boundary between the distinguished qualified portion and disqualified portion as the cut-off position. The cut-off position determining unit 27 transmits information related to the determined cut-off position to a steel-strip cutting device 152 in the testing process 15. The steel-strip cutting device 152 uncoils the steel-strip arranged at an uncoiler 153 up to the cut-off position by use of the uncoiler 153. The steel-strip cutting device 152 cuts the steel-strip at the cut-off position by transmitting a cut-off order command to a cutter 154.

Subsequently, a manufacturing condition determining unit 28 determines manufacturing conditions of a steel-strip product planned to be manufactured subsequently to the target steel-strip product (Step a20: manufacturing condition determining step). Specifically, by using the property estimating unit 23 as an inversion calculation unit to calculate manufacturing conditions from a given material property value, the manufacturing condition determining unit 28 calculates manufacturing conditions, by which the material properties match required specifications, and adds a difference between the calculated manufacturing conditions and the set manufacturing conditions, as a set correction term of the manufacturing conditions of the steel-strip product planned to be manufactured next, to the manufacturing conditions. For example, if coiling temperature is one of manufacturing conditions in a cooling process, and a coiling temperature in a representative mesh of a steel-strip is 550° C., the manufacturing condition determining unit 28 estimates material properties of virtual steel-strip products of five types having new manufacturing conditions with coiling temperature being 500° C., 525° C., 550° C., 575° C., and 600° C. The numerical values of the coiling temperature may be other values.

If tension strengths, which are the estimated material properties, are respectively 600 MPa, 620 MPa, 600 MPa, 580 MPa, and 560 MPa, and the required specification is 620 MPa, the manufacturing condition determining unit 28 selects the manufacturing condition with the coiling temperature of 525° C. that is closest to the required specification. Next, since the coiling temperature of the steel-strip product is 550° C., and the coiling temperature closest to the required specification is 525° C., if the coiling temperature for a steel-strip product to be manufactured next has been set at 560° C., the manufacturing condition determining unit 28 calculates the correction amount to be 525° C.-550° C.=−25° C. and sets the coiling temperature of the steel-strip product planned to be manufactured next to 560° C.-25° C.=535° C. In this embodiment, as a specific method of configuring an inversion calculation method, the method, in which the material property value closest to the required specification is retrieved from the plural manufacturing conditions around the manufacturing condition, has been described, but practically, the specific method is not limited to this method.

Figure 6:
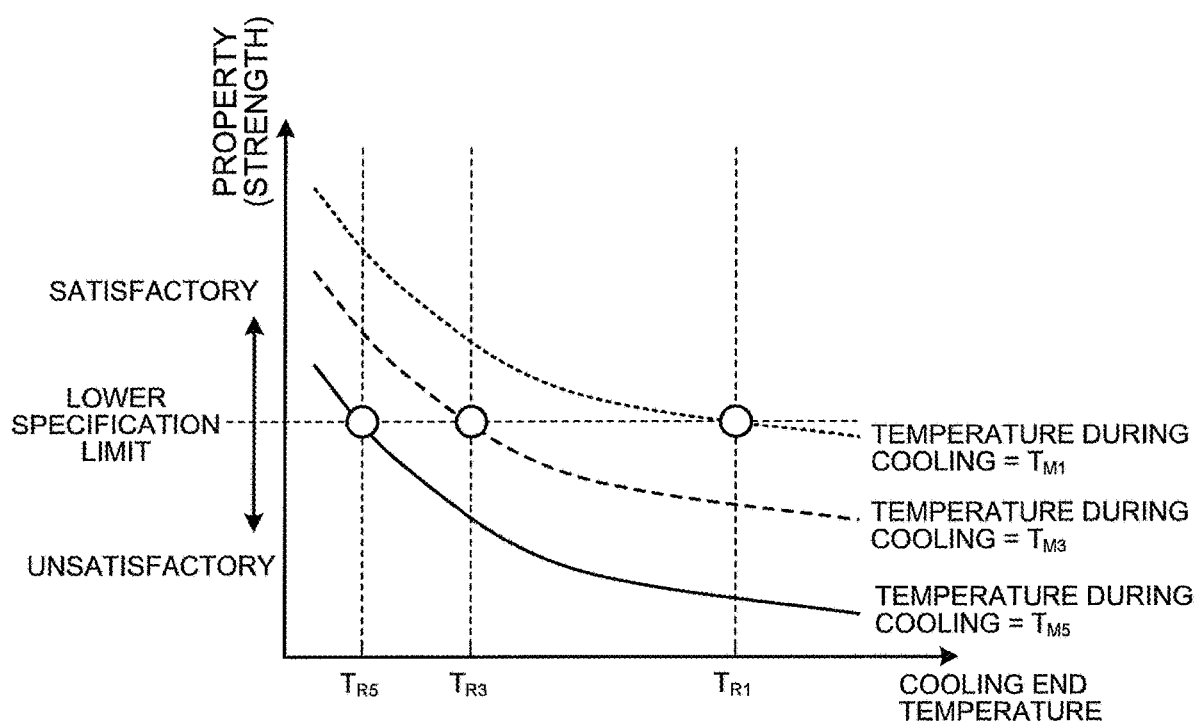
FIG. 6 is a diagram illustrating an example of relations between temperature after cooling and material properties under different temperatures during cooling.

Next, effects of this embodiment will be described. For that, firstly, focusing on a case where temperature during cooling measured in the manufacturing process 100 differs, relations between the temperature after cooling and the material properties will be described. FIG. 6 is a diagram illustrating an example of the relations between the temperature after cooling and the material properties for different values of the temperature during cooling, $T_{M1}$, $T_{M3}$, and $T_{M5}$. As illustrated in FIG. 6, the relations between the temperature after cooling and the material properties indicate a trend, for all of the temperatures during cooling=$T_{M1}$, $T_{M3}$, and $T_{M5}$, that the higher the temperature after cooling is, the lower the material property value is, but overall, when the temperature during cooling=$T_{M1}$, the material property value is large, and in order of the temperatures during cooling=$T_{M3}$ and $T_{M5}$, the material properties become smaller.

A case will now be considered, where quality of material properties is determined, by defining, from a correlation between the values of the temperature after cooling and the material properties, a temperature after cooling, $T_{R5}$, which satisfies a permissible value of material property value (required quality) and performing threshold processing of the temperature after cooling. In this case, the material property value will be determined as satisfactory if the temperature after cooling is not higher than $T_{R5}$, and as unsatisfactory if the temperature after cooling is higher than $T_{R5}$. However, actually, as illustrated in FIG. 6, the temperature during cooling also affects the material properties, and when the temperature during cooling=$T_{M5}$, if the temperature after cooling is higher than $T_{R5}$, the material property value is unsatisfactory. On the contrary, when the temperature during cooling=$T_{M3}$, even if the temperature after cooling is higher than $T_{R5}$, the material property value is satisfactory up to $T_{R3}$. When the temperature during cooling=$T_{M1}$, the material property value is satisfactory up to an even higher temperature after cooling of $T_{R1}$.

As described above, in determining quality of material properties by using the temperature after cooling as an index, without considering the temperature during cooling; when the temperature during cooling=$T_{M3}$ and the temperature after cooling is $T_{R5}$ to $T_{R3}$, or when the temperature during cooling=$T_{M1}$ and the temperature after cooling is $T_{R5}$ to $T_{R1}$, the material properties are determined to be unsatisfactory even though the material properties are actually satisfactory.

For comparison, the material property value estimating process illustrated in FIG. 4 was further executed, with two types of temperature being the manufacturing condition items, the two types of temperature being the temperature during cooling and the temperature after cooling, which were measured in the process of manufacturing a steel-strip product. FIG. 7(a) is a diagram illustrating a temperature distribution of the measured temperature during cooling in the steel-strip product, FIG. 7(b) is a diagram illustrating a temperature distribution of the measured temperature after cooling in the steel-strip product, and FIG. 7(c) is a diagram illustrating a material property value image of the steel-strip product, the material property value image obtained by the material property value estimating process. In FIG. 7(b), boundaries (cut-off positions) L31 and L33 between a qualified portion and a disqualified portion in the steel-strip product are illustrated, the qualified portion and the disqualified portion determined according to results of the above described determination of quality of the material properties with the temperature after cooling being an index. On the contrary, FIG. 7(c) illustrates cut-off positions L35 and L37 obtained by the material property value estimating process. As illustrated in FIG. 7, by the technique having the temperature after cooling as the index, end portions including qualified portions R31 and R33 having satisfactory material properties are cut-off, and thus the yield is reduced. Further, although illustration is omitted, on the contrary, the cut-off may be done with a disqualified portion having unsatisfactory material properties being left behind. In this case, the required quality is unable to be achieved.

The influence of the temperature during cooling on the relation between the temperature after cooling and the material properties has been described above with reference to FIG. 6 and FIG. 7, but there are factors influencing the material properties, other than the temperature during cooling and the temperature after cooling. Thus, in this embodiment, measured values of factors influencing the material properties as described above are collected as manufacturing condition items, and the material properties are estimated by use of the collected measured values or estimated values estimated from the measured values. Specifically, in this embodiment, the chemical composition per component, the slab thickness, the thickness between stands, the finishing thickness, the width between stands, the finishing width, the delivery temperature of reheating process, the entry temperature of cooling process, the temperature during cooling, and the temperature after cooling are the manufacturing condition items. Thereby, material properties of a steel-strip product are able to be estimated accurately over the entire region thereof.

In addition, in this embodiment, the measured values by the measuring devices in the reheating process 12, the rolling process 13, and the cooling process 14, which are performed while a target material is being conveyed, of the manufacturing process 100, are obtained while their measurement positions are being tracked. The material properties are then estimated per mesh corresponding to a measurement position of a measured value in the respective processes 12 to 14. Therefore, by performing threshold processing of the estimated material properties and distinguishing between a qualified portion and a disqualified portion in the steel-strip product, cut-off positions of the steel-strip product are able to be determined appropriately. Thereby, while the required quality is achieved, the decrease in the yield is able to be reduced.

In addition, in this embodiment, based on a difference between a material property value of a steel-strip product and a material property value defined by a required specification, a manufacturing condition of a steel-strip product planned to be manufactured subsequently to the target steel-strip product is corrected. Therefore, the more similar the properties of the target steel-strip product are to those of the steel-strip product to be manufactured next, the more appropriately the correction is able to be performed, such that manufacturing conditions satisfying the required specification of the material property value are obtained. Thereby, the part satisfying the required quality is increased and the yield is able to be improved.

The embodiment, to which the invention made by the inventors has been applied, has been described above, but the present invention is not limited by the description and drawings forming a part of disclosure of the present invention through this embodiment, and those configured by combining, as appropriate, the above described components are also included in the present invention. That is, any other embodiments, examples, operation techniques, and the like made by those skilled in the art or the like based on the embodiment are all included in the scope of the present invention.

According to the present invention, a material property value estimating method and a material property value estimating apparatus, which enable material properties of steel-strips to be estimated accurately are able to be provided. Further, a method of manufacturing a steel-strip, the method enabling decrease in yields to be reduced, is able to be provided.

REFERENCE SIGNS LIST

100 MANUFACTURING PROCESS
10 REFINING PROCESS
101 COMPONENT MEASURING DEVICE
11 CASTING PROCESS
111 THICKNESS METER
12 REHEATING PROCESS
123 THERMOMETER
13 ROLLING PROCESS
133, 135 THICKNESS AND WIDTH METER
137 MEASURING ROLL
14 COOLING PROCESS
143, 145, 147 THERMOMETER
15 TESTING PROCESS
151 TESTER
1 MATERIAL PROPERTY VALUE ESTIMATING APPARATUS
2 APPARATUS MAIN BODY
20 ARITHMETIC PROCESSING UNIT
21 MANUFACTURING CONDITION OBTAINING UNIT
23 PROPERTY ESTIMATING UNIT
25 VISUALIZING UNIT
27 CUT-OFF POSITION DETERMINING UNIT
30 ROM
31 PROPERTY ESTIMATING PROGRAM
40 RAM
50 BUS WIRING
3 INPUT DEVICE
4 DISPLAY DEVICE
5 ACTUAL VALUE COLLECTING DEVICE
6 ACTUAL RESULT DB
7 TRANSMISSION BUS

The invention claimed is:

1. A material property value estimating method of estimating a material property value of a target steel-strip product manufactured via at least one of a reheating process, a rolling process, and a cooling process, which are performed while a target material is being conveyed along a conveyance route, the material property value estimating method comprising:
 an estimating step of estimating a material property value of each of meshes dividing the target steel-strip product based on a measured value that has been measured once or more by a measuring device installed on the conveyance route, the measured value including at least a temperature of the target material; and a chemical composition per component of the target steel-strip product;
 an associating step of associating values of manufacturing condition items with the material property value, the values of manufacturing condition items including a chemical composition per component of a steel-strip product manufactured in the past and a measured value by the measuring device, the measured value collected in a manufacturing process of the steel-strip product manufactured in the past;
 a storage step of storing the associated values as an actual result data for each corresponding one of meshes dividing the steel-strip product; and
 a collecting step of collecting the measured value for each one of the meshes dividing the target steel-strip product, by obtaining the measured value by the measuring device in a manufacturing process of the target steel-strip product while tracking a measurement position of the measured value, wherein
 the estimating step includes:
  setting the chemical composition per component of the target steel-strip product and the measured value collected for each of the meshes as the values of manufacturing condition items related to the target steel-strip product; and
  estimating, for each of the meshes, by using the actual result data, the material property value corresponding to the values of manufacturing condition items related to the target steel-strip product;
 in the estimating step, a similarity between the values of manufacturing condition items related to the target steel-strip product and values of manufacturing condition items related to the steel-strip product manufactured in the past is calculated for each of the meshes, and the material property value corresponding to values of manufacturing condition items having the smallest similarity is estimated to be the material property value of each of the meshes,
 the meshes are three-dimensional meshes, and
 the estimating step elects the values of manufacturing condition items related to the target steel-strip product manufactured in the past for the meshes having same positions in a depth direction and calculates the similarity for the elected values of manufacturing condition items.

2. The material property value estimating method according to claim 1, further comprising a display processing step of generating a property-value distribution image representing a distribution state of the material properties in the target steel-strip product based on the estimated material property value for each of the meshes, and displaying the property-value distribution image on the display device.

3. The material property value estimating method according to claim 1, further comprising a distinguishment information outputting step of outputting distinguishably whether or not usable for a predetermined use, by performing threshold processing of the estimated material property value of each of the meshes.

4. The material property value estimating method according to claim 1, wherein the measured value includes a measured value of: thickness of the target material or target steel-strip in the rolling process measured by a dimension meter; or temperature of the steel-strip in the cooling process measured by a thermometer.

5. The material property value estimating method according to claim 1, wherein the estimating step calculates the similarity for the elected values of the manufacturing condition items by sequentially calculating a sum of squares of differences between the values of the manufacturing condition items related to the target steel-strip product and the values of the manufacturing condition items related to the steel-strip product manufactured in the past for each of the manufacturing condition items.

6. A method of manufacturing a steel-strip manufactured via at least one of a reheating process, a rolling process, and a cooling process, which are performed while a target material is being conveyed along a conveyance route, the method comprising:
- an estimating step of estimating a material property value of each of meshes dividing the steel-strip based on: a measured value that has been measured once or more by a measuring device installed on the conveyance route, the measured value including at least a temperature of the target material; and a chemical composition per component of the steel-strip; and
- a cutting step of determining a boundary position between a qualified portion and a disqualified portion in the steel-strip by performing threshold processing of the estimated material property value of each of the meshes, and cutting the steel-strip at the determined boundary position;
- an associating step of associating values of manufacturing condition items with the material property value, the values of manufacturing condition items including a chemical composition per component of a steel-strip product manufactured in the past and a measured value by the measuring device, the measured value collected in a manufacturing process of the steel-strip product manufactured in the past;
- a storage step of storing the associated values as an actual result data for each corresponding one of meshes dividing the steel-strip product; and
- a collecting step of collecting the measured value for each one of the meshes dividing the steel-strip product, by obtaining the measured value by the measuring device in a manufacturing process of the steel-strip product while tracking a measurement position of the measured value, wherein the estimating step includes:
- setting the chemical composition per component of the steel-strip product and the measured value collected for each of the meshes as the values of manufacturing condition items related to the steel-strip product; and
- estimating, for each of the meshes, by using the actual result data, the material property value corresponding to the values of manufacturing condition items related to the steel-strip product;

in the estimating step, a similarity between the values of manufacturing condition items related to the steel-strip product and values of manufacturing condition items related to the steel-strip product manufactured in the past is calculated for each of the meshes, and the material property value corresponding to values of manufacturing condition items having the smallest similarity is estimated to be the material property value of each of the meshes, the meshes are three-dimensional meshes, and the estimating step elects the values of manufacturing condition items related to the steel-strip product manufactured in the past for the meshes having same positions in a depth direction and calculates the similarity for the elected values of manufacturing condition items.

7. A method of manufacturing a steel-strip manufactured via at least one of a reheating process, a rolling process, and a cooling process, which are performed while a target material is being conveyed along a conveyance route, the method comprising:
- an estimating step of estimating a material property value of each of meshes dividing the a target steel-strip product based on: a measured value that has been measured once or more by a measuring device installed on the conveyance route, the measured value including at least a temperature of the target material; and a chemical composition per component of the target steel-strip product; and
- a manufacturing condition determining step of changing one or more settings of manufacturing conditions of the steel-strip, based on a difference between the estimated material property value of each of the meshes and a required specification of material property value;
- an associating step of associating values of manufacturing condition items with the material property value, the values of manufacturing condition items including a chemical composition per component of a steel-strip product manufactured in the past and a measured value by the measuring device, the measured value collected in a manufacturing process of the steel-strip product manufactured in the past;
- a storage step of storing the associated values as an actual result data for each corresponding one of meshes dividing the steel-strip product; and a collecting step of collecting the measured value for each one of the meshes dividing the target steel-strip product, by obtaining the measured value by the measuring device in a manufacturing process of the target steel-strip product while tracking a measurement position of the measured value, wherein the estimating step includes:
- setting the chemical composition per component of the target steel-strip product and the measured value collected for each of the meshes as the values of manufacturing condition items related to the target steel-strip product; and
- estimating, for each of the meshes, by using the actual result data, the material property value corresponding to the values of manufacturing condition items related to the target steel-strip product;

in the estimating step, a similarity between the values of manufacturing condition items related to the target steel-strip product and values of manufacturing condition items related to the steel-strip product manufactured in the past is calculated for each of the meshes, and the material property value corresponding to values of manufacturing condition items having the smallest similarity is estimated to be the material property value of each of the meshes, the meshes are three-dimensional meshes, and the estimating step elects the values of manufacturing condition items related to the target steel-strip product manufactured in the past for the meshes having same positions in a depth direction and calculates the similarity for the elected values of manufacturing condition items.

8. The method of manufacturing the steel-strip according to claim 7, wherein the measured value includes a measured value of: thickness of the target material or a target steel-strip in the rolling process measured by a dimension meter; or temperature of the steel-strip in the cooling process measured by a thermometer.

* * * * *